United States Patent
Rajala (10) Patent No.: US 10,806,634 B2
(45) Date of Patent: Oct. 20, 2020

(54) APPARATUS AND METHOD FOR APPLYING A FIRST WEB TO A BASE WEB IN A NONLINEAR PATTERN

(71) Applicant: Kimberly-Clark Worldwide, Inc., Neenah, WI (US)

(72) Inventor: Gregory John Rajala, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 16/334,980

(22) PCT Filed: Sep. 30, 2016

(86) PCT No.: PCT/US2016/054720
§ 371 (c)(1),
(2) Date: Mar. 20, 2019

(87) PCT Pub. No.: WO2018/063307
PCT Pub. Date: Apr. 5, 2018

(65) Prior Publication Data
US 2020/0016010 A1 Jan. 16, 2020

(51) Int. Cl.
*A61F 13/15* (2006.01)
*B29C 65/48* (2006.01)
(Continued)

(52) U.S. Cl.
CPC .. *A61F 13/15699* (2013.01); *A61F 13/15764* (2013.01); *B29C 65/48* (2013.01);
(Continued)

(58) Field of Classification Search
CPC .......... A61F 13/15699; A61F 13/15764; A61F 13/15609; A61F 13/15593;
(Continued)

(56) References Cited

U.S. PATENT DOCUMENTS 5,147,487 A 9/1992 Nomura et al.
5,766,411 A 6/1998 Wilson
(Continued)

FOREIGN PATENT DOCUMENTS

EP 2756831 A1 7/2014
JP 2002000644 A 1/2002
(Continued)

*Primary Examiner* — John L Goff, II
(74) *Attorney, Agent, or Firm* — Kimberly-Clark Worldwide, Inc.

(57) ABSTRACT

An applicator for and method of guiding a first web to a base web in a nonlinear pattern as the base web is advanced in a machine direction are disclosed. The applicator can include a support structure, a cantilever arm, a guide roller, and a connecting link. The cantilever arm can be supported by the support structure and moveable through a range of motion relative to the support structure in a cross machine direction. The guide roller can guide the first web onto the base web and can be pivotally mounted on the cantilever arm for pivotal movement of the guide roller with respect to the cantilever arm. The connecting link can be operatively coupled to the guide roller. Pivotal movement of the guide roller can be dependent on movement of the connecting link. Positioning of the guide roller in the cross machine direction can be dependent on movement of the cantilever arm.

17 Claims, 8 Drawing Sheets

(51) Int. Cl.
*B29C 65/00* (2006.01)
*B29L 31/48* (2006.01)

(52) U.S. Cl.
CPC .............. *B29C 66/20* (2013.01); *B29C 66/43* (2013.01); *A61F 2013/1591* (2013.01); *B29L 2031/4878* (2013.01)

(58) Field of Classification Search
CPC .............. A61F 2013/1591; B29C 66/22; B29C 66/221; B29C 66/223; B29C 66/225; B29C 66/229; B29C 66/2272; B29C 66/43
See application file for complete search history.

(56) References Cited

U.S. PATENT DOCUMENTS

| | | | |
|---|---|---|---|
| 6,284,081 | B1 * | 9/2001 | Vogt .................. A61F 13/15609 |
| | | | 156/163 |
| 7,000,260 | B2 | 2/2006 | Rajala et al. |
| 8,720,518 | B2 | 5/2014 | Rajala |
| 9,095,474 | B2 | 8/2015 | Nakano et al. |
| 9,271,878 | B2 | 3/2016 | Nakano et al. |
| 9,283,120 | B2 | 3/2016 | Fort |
| 2006/0185135 | A1 | 8/2006 | Yamamoto et al. |
| 2010/0107396 | A1 | 5/2010 | Yagyu et al. |
| 2010/0193135 | A1 | 8/2010 | Eckstein et al. |
| 2013/0261589 | A1 | 10/2013 | Fujkawa et al. |

FOREIGN PATENT DOCUMENTS

| | | |
|---|---|---|
| JP | 2003517978 A | 6/2003 |
| JP | 2013176494 A | 9/2013 |

* cited by examiner

APPARATUS AND METHOD FOR APPLYING A FIRST WEB TO A BASE WEB IN A NONLINEAR PATTERN

BACKGROUND

The present invention relates generally to an apparatus for and methods of applying a first web to a base web, and more particularly, to an apparatus for and a method of adhesively bonding a first web in a nonlinear pattern to a moving base web.

Absorbent articles, such as disposable diapers, training pants, adult incontinence articles and the like, generally include several different components that are bonded together. Typical absorbent articles include a bodyside liner, an outer cover, and an absorbent core disposed between the liner and outer cover. Besides the liner, the outer cover, and the absorbent core, typical absorbent articles also include a number of discrete components, e.g., fasteners, waist elastics, leg elastics. These discrete components of the article are often bonded to the bodyside liner and/or the outer cover. For example, it is known to adhesively bond leg elastics in a curved pattern to a continuous web of outer cover material or bodyside liner material.

Some known techniques for bonding leg elastics to a web moving at high line speeds are limited in the amount of displacement (e.g., the amount of amplitude in a curved pattern) that can be achieved. Thus, leg elastics in known absorbent articles produced at high line speeds are often straight or relatively straight. The leakage protection and the aesthetic appearance of known absorbent articles can be improved, however, by incorporating leg elastics with significant curvature along their lengths.

While some efforts to place leg elastics with significant amounts of displacement (i.e., curvature) onto a web at high line speeds have enjoyed some success, these known techniques still present challenges in terms of manufacturing reliability efficiency as machine line speeds continue to increase. These efforts have resulted in leg elastics being placed off target. Moreover, the deviation of the applied leg elastics from the target was not always the same. Some manufacturing issues, such as an elastic web breaking, cause the machine to be shut down, and thus, negatively impact machine line efficiency.

Figure 1:
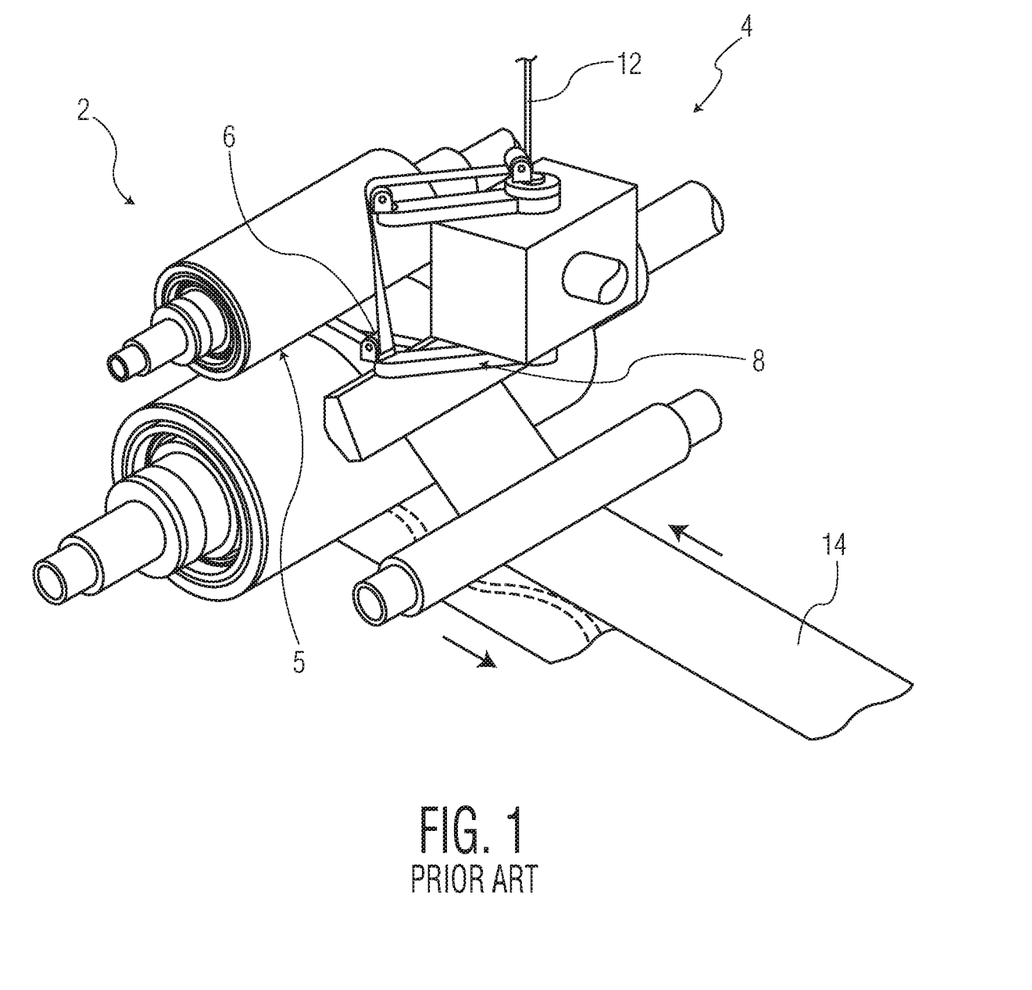
FIG. 1 illustrates a known apparatus of the prior art.

As an example, U.S. Pat. No. 8,720,518 issued to Rajala (the '518 patent) discloses an apparatus for bonding a ribbon in a nonlinear pattern to a web. FIG. 1 of the present application provides a representative figure from the '518 patent. The '518 patent discloses an apparatus 2 and applicator 4 for applying a first web 12 (such as an elastic ribbon) to a base web 14. The applicator 4 includes a guide roller 6 pivotally mounted to a lower cantilever arm 8. The guide roller 6 of the applicator 4 of the '518 patent pivots with respect to the lower cantilever arm 8 to provide the proper cross direction position of the first web 12 for the nip 5 based on the force provided by the first web 12 itself. This process works adequately where the angular accelerations of the pivotal movement of the guide roller 6 are relatively low (e.g., when running at lower machine line speeds or when the amplitude of the pattern of applying the first web 12 to the base web 14 is reduced). However, when angular accelerations of this pivotal movement of the guide roller 6 are increased (e.g., when running at increased machine line speeds and/or increased amplitudes of the pattern for applying the first web 12 to the base web 14), the forces in the first web 12 may surpass the tensile strength of the first web 12 and cause the first web 12 to break. Alternatively, the actual pivotal movement of the guide roller 6 may lag behind the desired pivotal movement of the guide roller 6 when faced with increased demands for angular accelerations of the guide roller 6 in the situations of high line speeds and/or larger amplitudes of the pattern of applying the first web 12 to the base web 14. Such a lag can result in inaccurate placement of the first web 12 with respect to the desired pattern on the base web 14.

As a result, it is desirable to provide an apparatus for and method of applying a first web in a nonlinear manner to a base web that can provide greater capabilities in providing a wider amplitude in a pattern of the first web to a base web and/or at greater machine line speeds. It is also desirable to provide an apparatus for and method of applying a first web in a nonlinear manner to a base web that provides the desired pattern with more reliability and operates under more favorable conditions for the first web.

SUMMARY

In one aspect, an applicator for guiding a first web to a base web as the base web is advanced in a machine direction is provided. The applicator can include a support structure and a cantilever arm. The cantilever arm can be supported by the support structure and can be moveable through a range of motion relative to the support structure in a cross machine direction. The applicator can include a guide roller for guiding the first web onto the base web. The guide roller can be pivotally mounted on the cantilever arm for pivotal movement of the guide roller with respect to the cantilever arm. The applicator can further include a connecting link operatively coupled to the guide roller. Pivotal movement of the guide roller can be dependent on movement of the connecting link. Positioning of the guide roller in the cross machine direction can be dependent on movement of the cantilever arm.

In another aspect, a method for guiding a first web to a base web in a nonlinear pattern is provided. The method can include providing the first web and providing the base web. The method can also include advancing the base web in a machine direction. The method can include providing an applicator. The applicator can include a cantilever arm supported by the support structure and moveable through a range of motion relative to the support structure in a cross machine direction. The guide roller can also include a guide roller configured for engaging the first web and a connecting link operatively coupled to the guide roller. Pivotal movement of the guide roller can be dependent on movement of the connecting link. The method can additionally include guiding the first web to the base web in a nonlinear pattern by moving the guide roller through a range of motion relative to the support structure in a cross machine direction by moving the cantilever arm and moving the connecting link in a machine direction to pivot the guide roller with respect to the cantilever arm to guide the first web to the base web.

DETAILED DESCRIPTION

Figure 2:
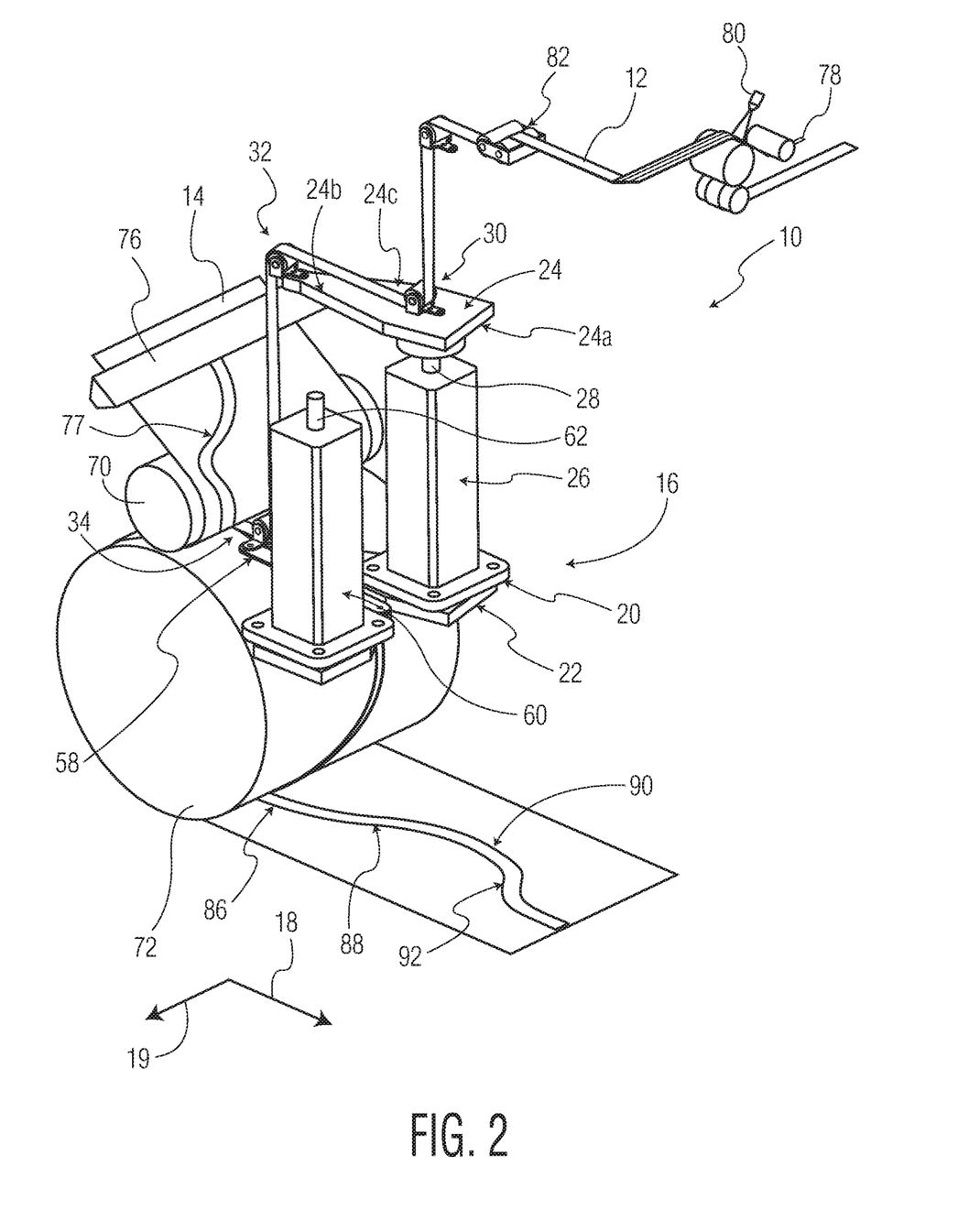
FIG. 2 illustrates a top perspective view of an exemplary embodiment of an apparatus for applying a first web to a base web in a nonlinear pattern.

Referring to FIG. 2, an apparatus 10 for applying a first web 12 to a base web 14 is shown. The apparatus 10 can include an applicator 16 for guiding the first web 12 to the base web 14 as the base web 14 is advanced in a machine direction 18. The applicator 16 can include a support structure 20. Support structure 20 can include framework that can provide stability and mounting for the applicator 16. The applicator 16 can also include a cantilever arm 22 that is supported by the support structure and moveable through a range of motion relative to the support structure 20 in a cross machine direction 19. In some embodiments, cantilever arm 22 can be referred to as a lower cantilever arm 22, as the applicator 16 can also include an upper cantilever arm 24. The lower cantilever arm 22 and the upper cantilever arm 24 can be connected to a pivot motor 26, and specifically, a pivot shaft 28 forming part of the pivot motor 26. In a preferred embodiment, the pivot motor 26 can be a servo motor.

As depicted in FIG. 2, the lower cantilever arm 22 can be disposed below the pivot motor 26 and the upper cantilever arm 24 can be disposed above the pivot motor 26. Each of the cantilever arms 22, 24 can include an attachment end 22a, 24a, a free end 22b, 24b, and an intermediate portion 22c, 24c, respectively. The intermediate portion 22c, 24c of the cantilever arms 22, 24, respectively, extends between the attachment end 22a, 24a and the free end 22b, 24b, respectively. The attachment end 22a, 24a of each of the lower and upper cantilever arms 22, 24, respectively, is coupled to the pivot shaft 28 of the pivot motor 26 such that rotation of the pivot shaft 28 results in conjoint rotation of the lower and upper cantilever arms 22, 24. The cantilever arms 22, 24 can extend outward from the pivot shaft 28. In some embodiments, the lower cantilever arm 22 can be the same length as the upper cantilever arm 24. However, in other embodiments, the lower cantilever arm 22 can be of a different length than the upper cantilever arm 24. For example, in one embodiment, the lower cantilever arm 22 can be longer than the upper cantilever arm 24. In one such embodiment, the lower cantilever arm 22 can be about 10 inches in length and the upper cantilever arm can be about 8.5 inches in length.

The applicator 16 can include one or more guide rollers. In the embodiment depicted in FIGS. 2-3A, the applicator 16 can include three guide rollers 30, 32, 34. A first guide roller 30 can be mounted on the upper cantilever arm 24 adjacent the attachment end 24a of the upper cantilever arm 24. A second guide roller 32 can be mounted on the upper cantilever arm 24 adjacent the free end 24b of the upper cantilever arm 24. A third guide roller 34 can be mounted on the lower cantilever arm 22 adjacent the free end 22b of the lower cantilever arm 22.

Figure 3:
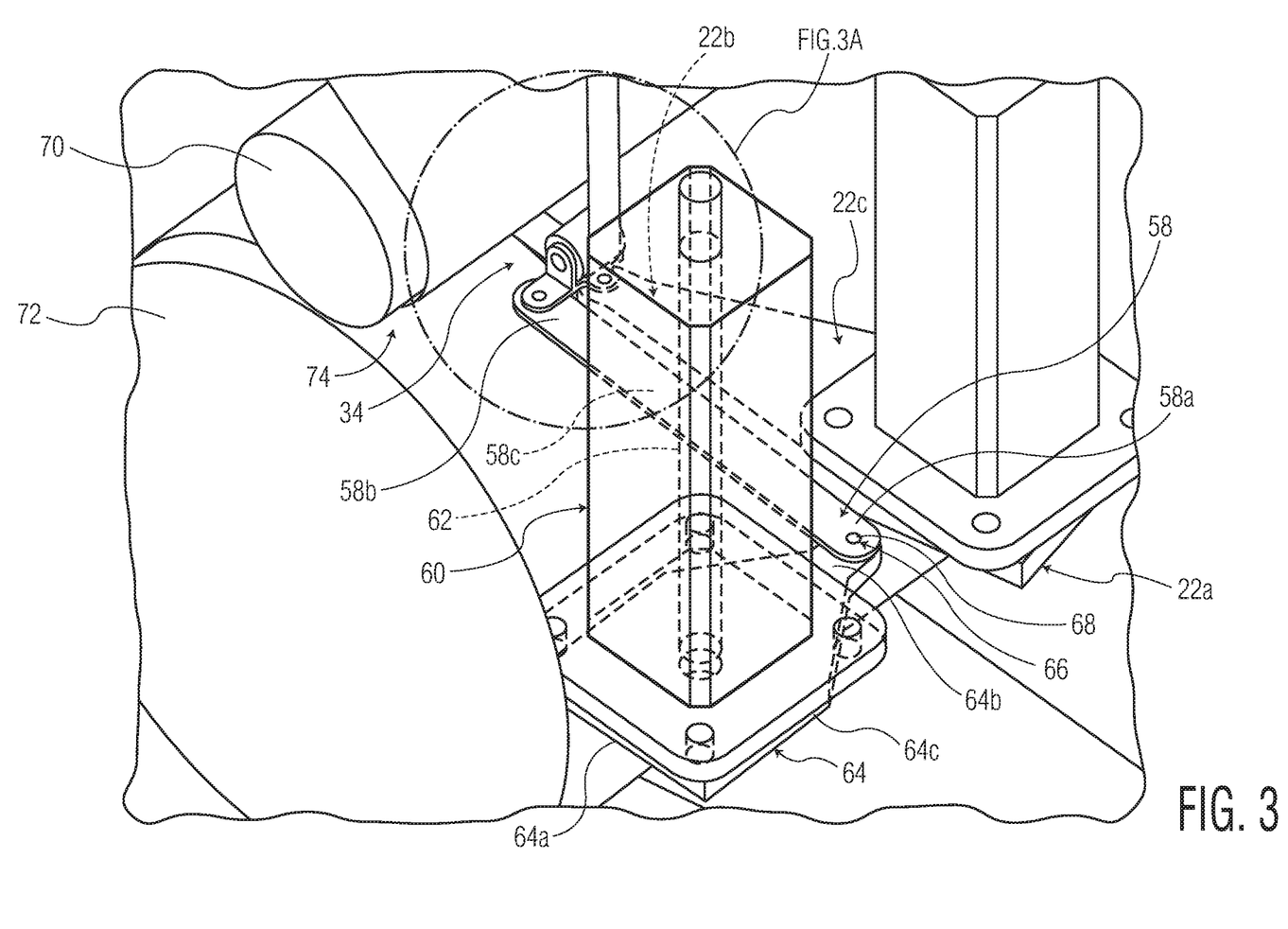
FIG. 3 illustrates a detailed, perspective view of select components of the embodiment displayed in FIG. 2.
Figure 3A:
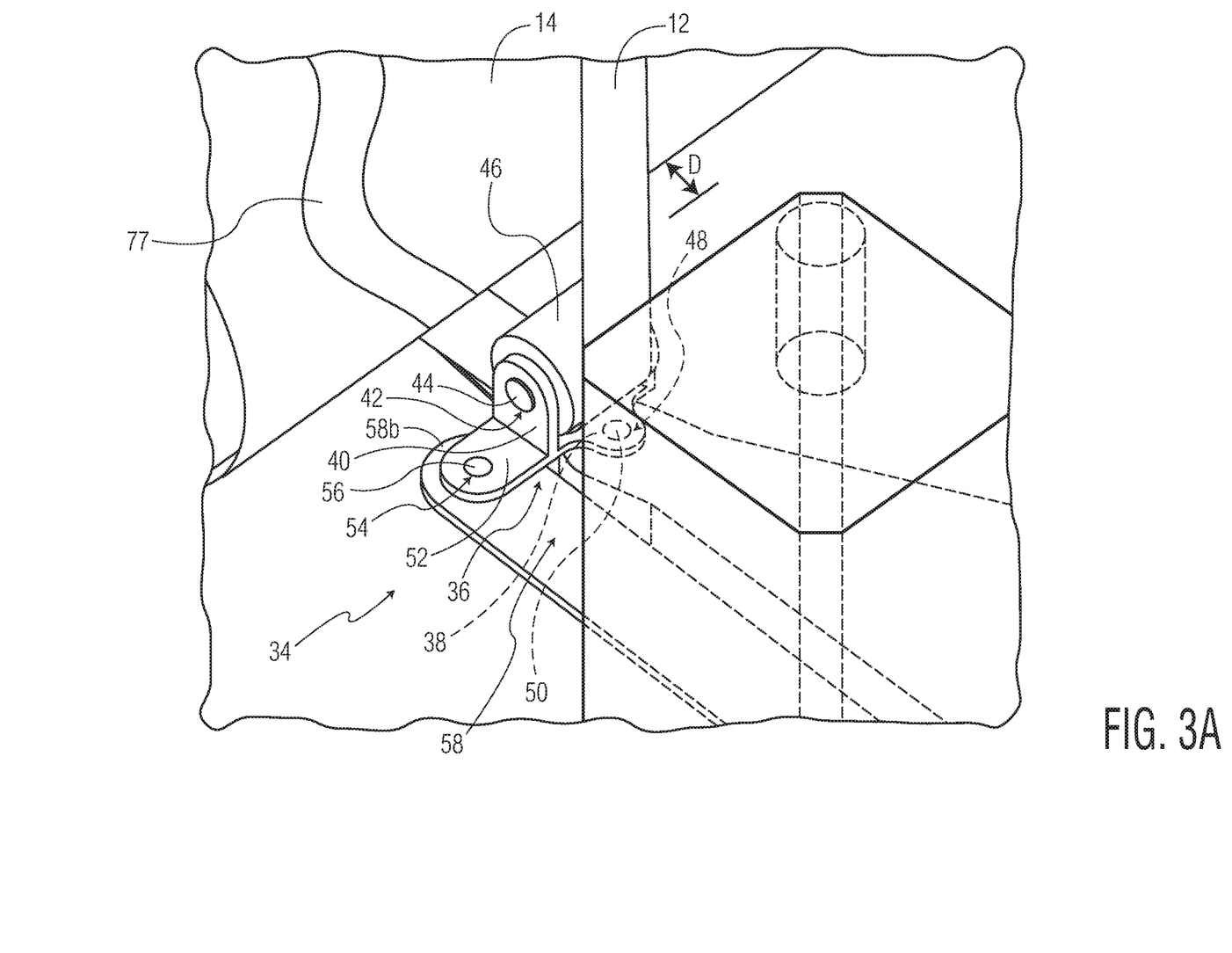
FIG. 3A illustrates a detailed perspective view taken along line 3A-3A of FIG. 3.

As best depicted in FIGS. 3 and 3A, the third guide roller 34 is pivotally mounted on the lower cantilever arm 22 adjacent the free end 22b of the lower cantilever arm 22 such that the guide roller 34 can pivot with respect to the lower cantilever arm 22. The third guide roller 34 can include a bracket 36 including a base plate 38 and a pair of sidewalls 40 (only one sidewall 40 labeled in FIG. 3A for clarity). Each of the sidewalls 40 can include an aperture 42 (only one aperture 42 being labeled in FIG. 3A for clarity) for receiving and thereby mounting a shaft 44 to the bracket 36. A roller 46 can be rotatably mounted to the shaft 44. The base plate 38 can also include an opening 48. A pivot pin 50 can be received through the opening 48 in the base plate 38 to pivotally mount the third guide roller 34 to the lower cantilever arm 22, as discussed above. That is, the third guide roller 34 can pivot with respect to the lower cantilever arm 22 about the pivot pin 50. In the illustrated embodiment, the roller 46 is a cylindrical roller, but it is contemplated that the roller 46 can have any other suitable shapes (e.g., spool-like, hourglass, prolate spheroid, truncated prolate spheroid) without departing from the scope of this disclosure.

As illustrated in FIG. 3A, the bracket 36 for third guide roller 34 can also include a flange 52. Flange 52 can be in the same plane as the base plate 38 and can extend beyond one wall 40 of the pair of side walls 40 of the bracket 36. Flange 52 can include an opening 54. A pivot pin 56 can be received through the opening 54 in the flange 52 to pivotally mount the flange 52 to a connecting link 58, as will be discussed in further detail below.

As illustrated in FIG. 3, the applicator 16 can also include a connecting link 58. The connecting link 58 can be operatively coupled to the third guide roller 34. The connecting link 58 can include a proximal end 58a, a distal end 58b, and an intermediate portion 58c extending between the proximal end 58a and the distal end 58b. As noted above, the pivot pin 56 can be received in the opening 54 of the flange 52 of bracket 36 and can pivotally mount the connecting link 58 to the flange 52 of bracket 36. As illustrated in FIG. 3A, the pivot pin 56 can be received by an opening (not pictured) near the distal end 58b of the connecting link 58. In this embodiment, the connecting link 58 can be coupled to the bracket 36 for the third guide roller 34, such that the pivotal movement of the third guide roller 34 is dependent upon movement of the connecting link 58.

Referring to FIGS. 2 and 3, the applicator 16 can additionally include a guide motor 60 including a guide shaft 62. In a preferred embodiment, the guide motor 60 can be a servo motor. The guide shaft 62 can be operatively connected to the connecting link 58 such that rotation of the guide shaft 62 can move the connecting link 58 in the machine direction 18. For example, in one embodiment, the guide shaft 62 can be coupled to a guide arm 64. The guide arm 64 can include an attachment end 64a, a free end 64b, and an intermediate portion 64c extending between the attachment end 64a and the free end 64b. The guide arm 64 can be coupled to the guide shaft 62 adjacent the attachment end 64a of the guide arm 64. The proximal end 58a of the connecting link 58 can be coupled to the guide arm 64 adjacent the free end 64b of the guide arm 64. As illustrated in FIG. 3A, the proximal end 58a of the connecting link 58 can include an opening 66 for receiving a pivot pin 68 to couple the connecting link 58 to the guide arm 64. From this coupling, the guide arm 64 can be operably connected to the guide shaft 62 and the connecting link 58. Thus, the guide shaft 62 can be coupled to the connecting link 58. As will be discussed in further detail below, in this embodiment, rotation of the guide shaft 62 can thus move the connecting link 58 in a machine direction 18, which in turn, controls the pivotal movement of the third guide roller 34 guiding the first web 12.

With reference again to FIGS. 2 and 3, the apparatus 10 also includes a pair of anvil rolls 70, 72 that together define a nip 74 (labeled in FIG. 3). The anvil rolls 70, 72 are configured to apply a predetermined pressure to the first web 12 and base web 14 as they pass through the nip 74. The pressure applied to the first web 12 and base web 14 at nip 74 can be varied by changing the relative positions of the rolls 70, 72.

The rolls 70, 72 rotate in opposite directions, as indicated by the arrows in FIG. 1, to draw the first web 12 and the base web 14 into the nip 74. Each of the rolls 70, 72 is operable independently from the other and are driven (i.e., rotated) by suitable drive means, such as, for example, electric motors (not shown). As a result, the rotational speed of the rolls 70, 72 (as measured at the rolls' outer surface) can be the same or can differ. That is, the rolls 70, 72 can operate at the same or different rotational speeds.

Each of the rolls 70, 72 in the illustrated embodiment is cylindrical with a smooth outer surface. It is contemplated, however, that one or both of the rolls 70, 72 can have shapes other than cylindrical and that the outer surface may be other than smooth (i.e., patterned). In addition, the rolls 70, 72 can be formed from any suitable, durable material, such as, for example, hardened metal or steel, hardened rubber, resin-treated cotton, or polyurethane. The rolls 70, 72 can be formed from the same material or different materials. In the illustrated embodiment, for example, the roll 70 is a steel roll covered with silicone rubber having a 55A to 70A Shore Durometer to facilitate release of any adhesive that may contact the roll 70, and the roll 72 is a hardened steel roll.

The temperature of the outer surface of at least one of the rolls 70, 72 can be controlled to heat or cool the respective roll. In one suitable embodiment, the outer surface of at least one of the rolls 70, 72 is cooled to inhibit adhesive from bonding to or otherwise adhering to the outer surface of the roll. In another suitable embodiment, the outer surface of at least one of the rolls 70, 72 is heated to enhance bonding between first web 12 and the base web 14.

As illustrated in FIG. 2, the apparatus 10 can also comprise an adhesive applicator 76 for applying adhesive in a nonlinear pattern to the base web 14. It is understood that any suitable adhesive applicator can be used to apply the adhesive to the base web 14. It is contemplated, however, that adhesive can be applied to the first web 12 instead of or in addition to the base web 14.

The first web 12 can be formed from any suitable material including, but not limited to, wovens, nonwovens, films, foams, or combinations thereof. The material can be stretchable, non-stretchable, elastic or inelastic. In one suitable embodiment, the first web 12 is an elastomeric material suitable for use as leg elastics in absorbent articles.

As seen in FIG. 2, the illustrated first web 12 can be an elastomeric laminate comprising one or more elastic materials 78 (such as LYCRA strands). The apparatus 10 can include an adhesive applicator 80 that applies an adhesive to the first web 12 and/or the elastic material 78. The first web 12 can then be folded and pass through a nip 82 to further couple the elastic material 78 to the first web 12. Instead of folding the first web 12 over the elastic material 78 as depicted in FIG. 2, it is contemplated that the first web 12 could include two separate webs with the elastic material 78 sandwiched between the two sheets. It is also contemplated that one of the first and second sheets or the folding of the first web to sandwich the elastic material 78 can be omitted. In other suitable embodiments, the first web 12 can be formed from spunbond laminates (SBL), necked bonded laminates (NBL), and spunbond-meltblown-spunbond (SMS) nonwovens, which are also suitable materials for use as leg elastics in absorbent articles.

In one suitable embodiment, the base web 14 comprises a material suitable for use as an outer cover of absorbent articles. As one example, the outer cover material may be a multi-layered laminate structure to provide desired levels of extensibility as well as liquid impermeability and vapor permeability. For example, the outer cover may be a two-layer construction, including an outer layer constructed of a vapor permeable material and an inner layer constructed of a liquid impermeable material, with the two layers being secured together by a suitable adhesive. It is understood, however, that the outer cover material can have more or fewer layers (e.g., a single layer plastic film).

In another embodiment, the base web 14 can comprise a material suitable for use as a bodyside liner of absorbent articles. The bodyside liner material can be a material that is suitably pliable, soft feeling, and nonirritating to the wearer's skin. The bodyside liner material should be sufficiently porous to be liquid permeable to thereby permit liquid (e.g., urine) to readily penetrate through its thickness. Suitable bodyside liner materials can be manufactured from a wide selection of web materials.

In use, the base web 14 can be provided from a roll (or other suitable web source) to the adhesive applicator 76 where adhesive 77 is applied in a nonlinear pattern to the base web 14 (FIGS. 2 and 3). In one embodiment, the adhesive 77 can be applied to the base web 14 in a nonlinear pattern using an adhesive applicator 76 that includes a rotary valve, as taught by International Patent Application PCT/US15/52919 of Kimberly Clark Worldwide, Inc., which is incorporated by reference in its entirety. In one suitable embodiment, the base web 14 is traveling at a high line speed. As used herein, high line speed refers to a line speed greater than about 600 feet per minute. In some embodiments, the line speed can be greater than about 800 feet per minute, or greater than about 1000 feet per minute. The adhesive 77 is heated to a suitable temperature and driven to the adhesive applicator 76 at a suitable pressure by an adhesive source. In an "on position" of the adhesive applicator 76, adhesive 77 is driven through a housing of the adhesive applicator 76 and onto the base web 14 in the desired nonlinear pattern of adhesive 77 (e.g., a curved pattern).

After the adhesive 77 is applied to the base web 14 by the adhesive applicator 76, the base web 14 is fed to the nip 74 defined by the pair of opposed rolls 70, 72. As described in more detail below, the first web 12 is laid over the adhesive 77 applied to the base web 14 prior to the web 14 entering the nip 74.

As illustrated in FIG. 2, the first web 12 is fed to the applicator 16 by a source of the first web 12 (such as a roll). The applicator 16 guides and applies the first web 12 to the base web 14 in a nonlinear pattern that substantially matches the nonlinear pattern along which the adhesive 77 was applied to the base web 14 such that the first web 12 overlies and covers the adhesive 77. More specifically, the first web 12 is fed past the first guide roller 30 and generally parallel to the upper cantilever arm 24 to the second guide roller 32. From the second guide roller 32, the first web 12 is fed downward (as viewed in FIG. 2) to the pivotable third guide roller 34.

Preferably, the first web 12 can be fed through the guide rollers 30, 32, 34 under tension which causes the first web 12 to stretch. In one suitable embodiment, the first web 12 is under tension of about 0.1 pound to about 1 pound per linear inch of width of the first web 12. It is understood, however, that the tension force applied to first web 12 can be different than disclosed herein.

The third guide roller 34 is spaced from the second guide roller 32 by a vertical distance. The vertical distance can be selected to facilitate proper alignment of the first web 12 as it is fed to the third guide roller 34 and to inhibit twisting or bunching of the first web 12 during movement of the third guide roller 34 relative to the second guide roller 32, which is mounted to the upper cantilever arm 24 in a non-pivoting manner. In one suitable configuration, the vertical distance between the third guide roller 34 and the second guide roller 32 is approximately 10 times the width of the first web 12.

In the illustrated embodiment, the first web 12 is wrapped around approximately 90 degrees of the circumference of each of the guide rollers 30, 32, 34. In other words, the first web 12 extends around about a quarter of the circumference of the guide rollers 30, 32, 34 as it passes over the respective guide roller. It is understood that the first web 12 can be wrapped around more or less of the circumference of one or more of the guide rollers 30, 32, 34 by changing the angle at which the first web 12 is fed to the respective guide roller (i.e., the approach angle of the first web 12).

The placement of the first web 12 onto the base web 14 can be accurately controlled by the applicator 16. Specifically, the position of the third guide roller 34 is controlled to accurately guide and apply the first web 12 to the base web 14 by controlling the cross direction position of the third guide roller 34 with respect to the nip 74 by movement of the lower cantilever arm 22 and by controlling the angle θ of the third guide roller 34 with respect to the nip 74 by movement of the connecting link 58 (as angle θ being labeled in FIG. 4).

Figure 4:
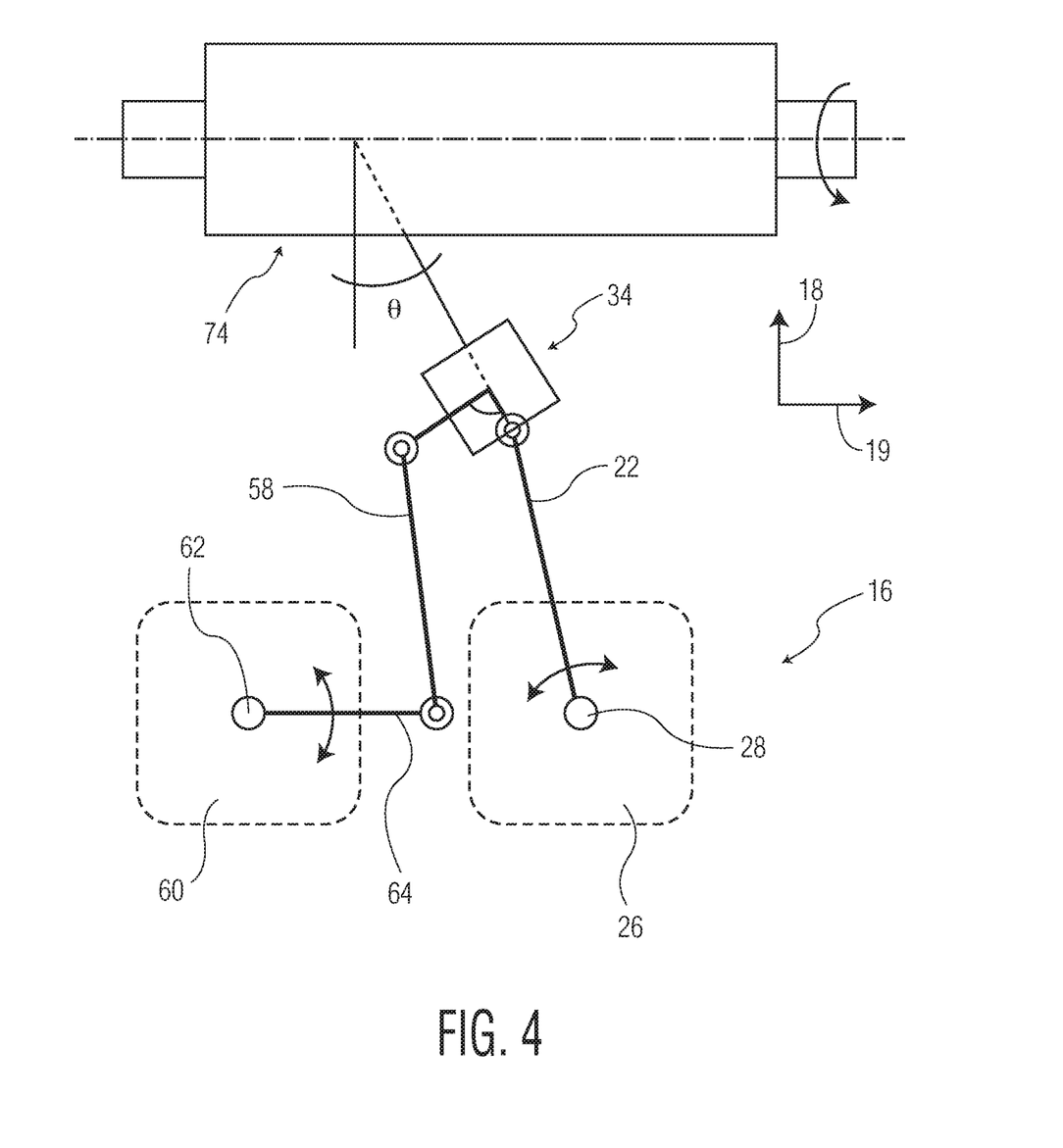
FIG. 4 illustrates an exemplary schematic of how the guide roller of the embodiment of FIG. 2 pivots and moves in the cross direction.

As illustrated in the schematic of FIG. 4, movement of the lower cantilever arm 22 to direct the third guide roller 34 to move in a cross direction 19 can be controlled by rotating the pivot shaft 28 of the pivot motor 26, either clockwise or counter-clockwise. The movement of the connecting link 58 can be controlled by the rotational movement of the guide shaft 62 of the guide motor 60, either clockwise or counter-clockwise, which rotates the guide arm 64 to which the connecting link 58 is coupled, as discussed above. The machine direction movement 18 of the connecting link 58 controls the angle θ of the third guide roller 34 with respect to the nip 74. Although a servo motor is preferred for pivot motor 26 and guide motor 60, servo motors may be substituted with cam boxes driven from any suitable drive source including, for example, lineshafts, AC or DC variable speed drives and motors. It is contemplated that programmable controllers connected to pivot motor 26 and guide motor 60 cause the pivot shaft 28 and guide shaft 62 to perform suitable respective back and forth motions in synchronism with the advancement of base web 14.

Figure 5A:
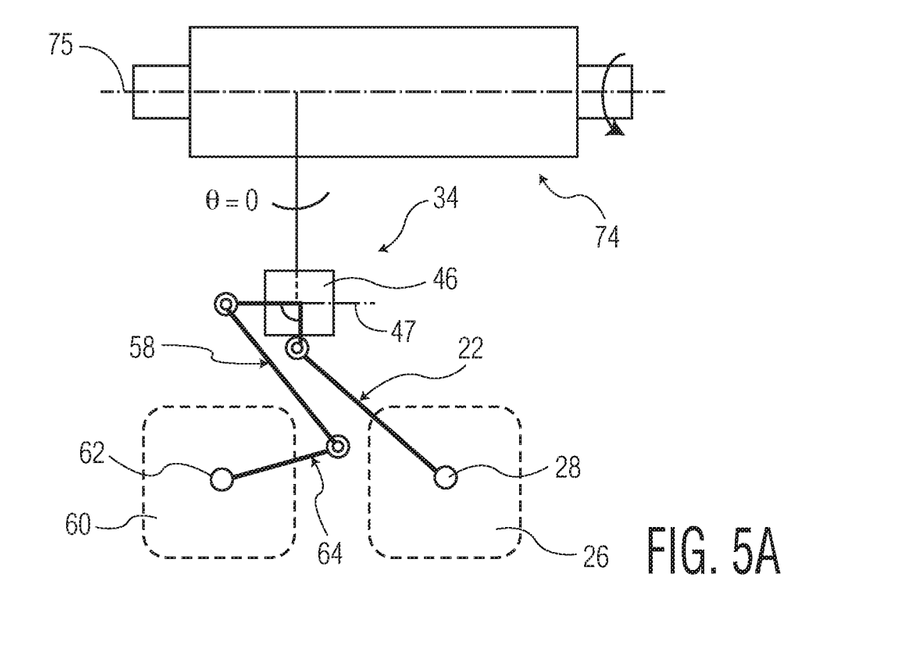
FIGS. 5A-5D illustrates an exemplary schematic of how the guide roller of the embodiment of FIG. 2 pivots and moves in a cross direction to move the first web from an initial cross direction position in the nip to a final cross direction position in the nip.
Figure 5B:
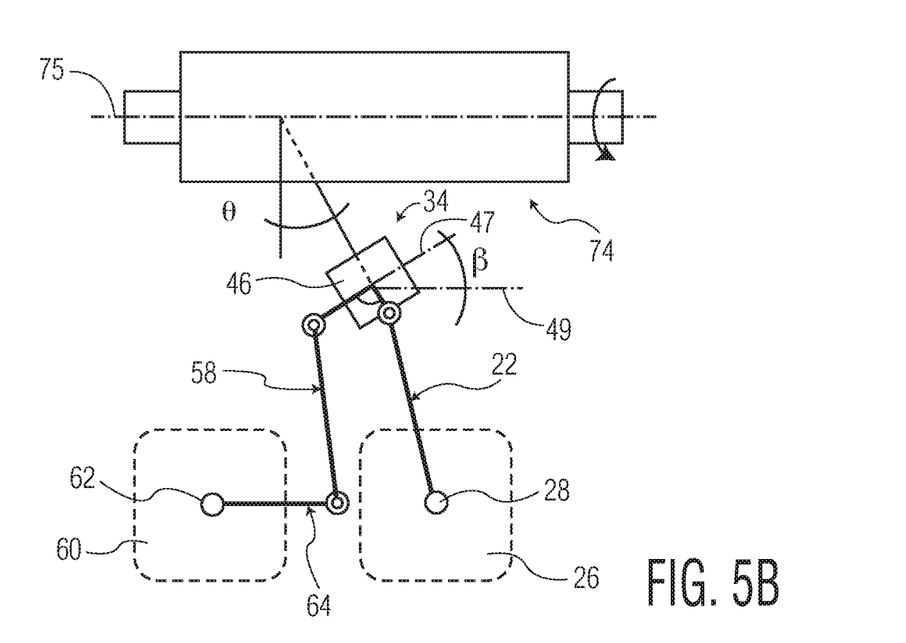

FIGS. 5A-5B illustrate how the third guide roller 34 can move in a cross direction 19 position with respect to the nip 74 as well as pivotally move with respect to the lower cantilever arm 22 such that the angle θ of the first web 12 entering the nip 74 can change. Starting first with FIG. 5A, the angle θ is 0° with respect to a line perpendicular to the nip 74. In other words, an axis 47 of the roller 46 of the third guide roller 34 is parallel to an axis 75 defined by the nip 74. The cross direction position of the third guide roller 34 is, as viewed in FIG. 5A, is in a position on the left side of the nip 74.

Moving to FIG. 5B, as time passes the applicator 16 controls the third guide roller 34 to accurately guide and position the first web (not shown for clarity) to the nip 74 to form the desired nonlinear pattern of the first web 12 on the base web 14 (not shown for clarity). This is accomplished by the pivot motor 26 rotating the pivot shaft 28 in a clockwise direction, which in turn rotates lower cantilever arm 22 in a clockwise direction. Rotating lower cantilever arm 22 in a clockwise direction moves the third guide roller 34 in a cross direction 19 to the right when viewing FIG. 5B. To maintain the angle θ to match the instantaneous angle of the first web 12, the guide motor 60 rotates the guide shaft 62 in a clockwise direction, which in turn rotates guide arm 64 in a clockwise direction, and which in turn rotates connecting link in a clockwise direction and moves the connecting link 58 in a machine direction 18 downward as viewed in FIG. 5B. The axis 47 of the roller 46 of the third guide roller 34 forms an angle ß with a line 49 parallel to the nip axis 75. Angle ß can equal angle θ, which defines the angle of the first web 12 entering the nip 74. By purposefully pivoting the guide roller 34 to manage the angle θ of the guide roller 34 with respect to the nip 74 as the guide roller 34 moves in a cross direction 19, the tension on the first web 12 is beneficially reduced helping to reduce the risk that the first web 12 breaks or is under unnecessary stress.

Figure 5C:
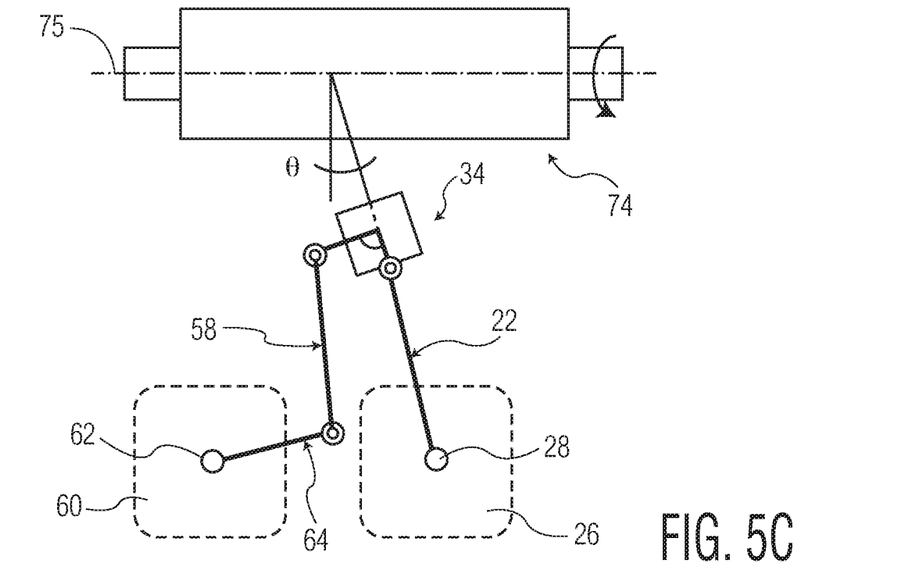

In FIG. 5C, more time passes and the first web 12 migrates to the new cross directional position of the third guide roller 34 as noted above in FIG. 5B. The guide motor 60 then rotates guide shaft 62 counter-clockwise, which in turn rotates the guide arm 64 counter-clockwise, which moves the connecting link 58 in a machine direction 18 upwards when viewing FIG. 5C. With such movement of the connecting link 58, the angle θ is reduced to coincide with the instantaneous angle of the first web 12 (not shown). Again, by purposefully pivoting the guide roller 34 to manage the angle θ of the guide roller 34 with respect to the nip 74 as the guide roller 34 moves in a cross direction 19, the tension on the first web 12 is beneficially reduced helping to reduce the risk that the first web 12 breaks or is under unnecessary stress.

Figure 5D:
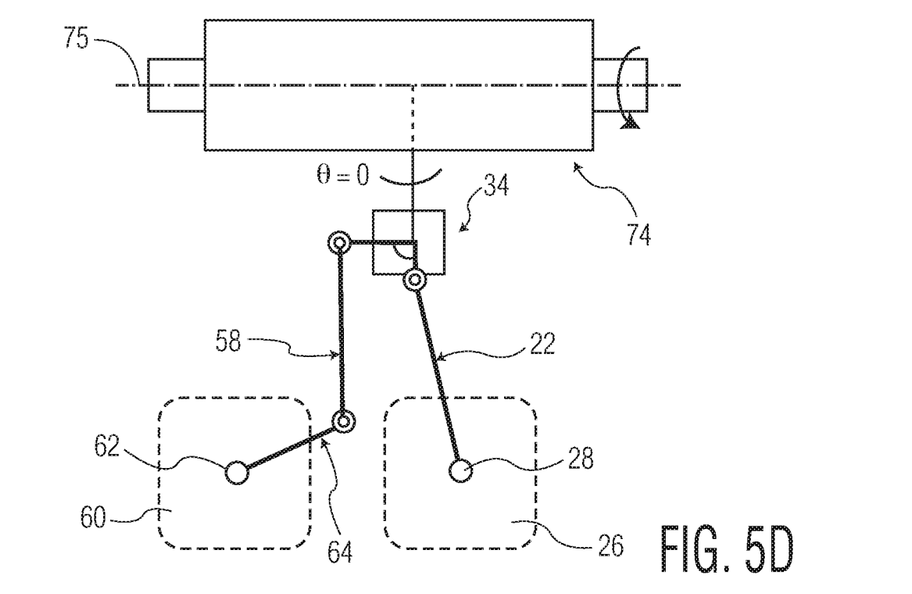

In FIG. 5D, sufficient time has passed for the first web 12 to migrate to a final cross directional position in line with the third guide roller 34. As such, the guide motor 60 rotates guide shaft 62 counter-clockwise, which in turn rotates the guide arm 64 counter-clockwise, which moves the connecting link 58 in a machine direction 18 upwards when viewing FIG. 5C. With such movement of the connecting link 58, the angle θ is reduced to 0° with respect to a line perpendicular to the nip 74 and coincides with the instantaneous angle of the first web 12 (not shown).

The applicator 16, and specifically, the third guide roller 34 can return to the position as shown in FIG. 5A. To do so, the lower cantilever arm 22 can rotate in a counter-clockwise direction through the rotation of the pivot shaft 28 in a counter-clockwise direction. As such, the lower cantilever arm 22 can rotate in a reciprocating arc motion in the process of guiding the first web 12 to the base web 14. The third guide roller 34 can also be pivoted with respect to the lower cantilever arm 22 in returning to the position as shown in FIG. 5A by first rotating the guide shaft 62 in a counter-clockwise direction as the third guide roller 34 moves cross directionally to the left and then by rotating the guide shaft 62 in a clockwise direction as the first web 12 aligns with the third guide roller to maintain the angle θ to match the instantaneous angle of the first web 12 as described above.

Figure 6:
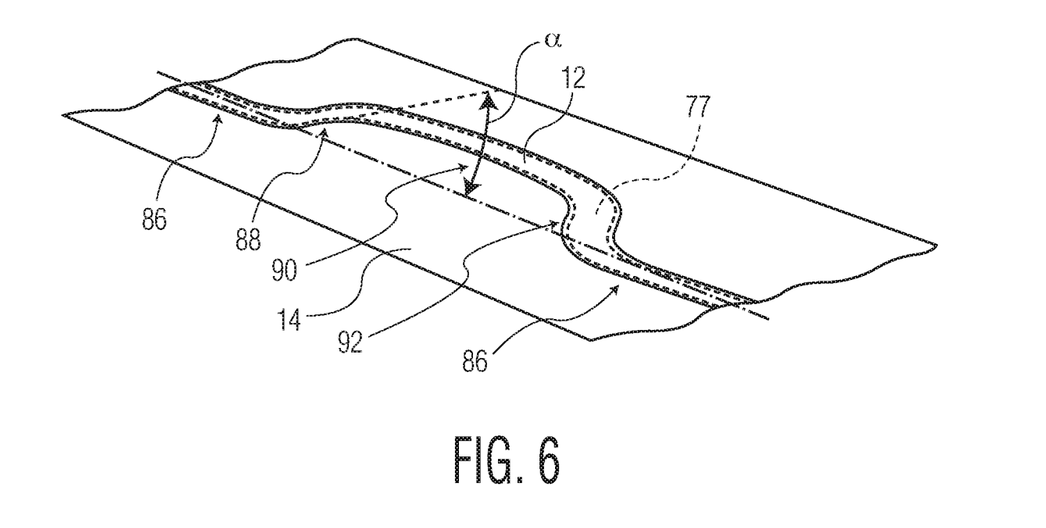
FIG. 6 illustrates a perspective view of a portion of a base web showing the first web adhered thereto in a nonlinear pattern.

The apparatus 10 for and method of guiding and applying the first web 12 to the base web 14 in a nonlinear pattern as described above can be in various configurations. In one suitable embodiment, as illustrated in FIGS. 2 and 6, the applicator 16 can provide a generally sinusoidal pattern of the first web 12 on the base web 14. For example, as the base web 14 is running, the applicator 16 can pause the cross directional and pivotal movement of the third guide roller 34 to provide a generally linear segment 86 of the first web 12 on the base web 14. Such a generally linear segment 86 of the nonlinear pattern of the first web 12 on the base web 14 can be provided when the third guide roller 34 is in the position as described above with respect to FIG. 5C. When the third guide roller 34 begins to move cross directionally with respect to the nip 74 and pivotally with respect to the lower cantilever arm 22 as described above with respect to FIGS. 5B and 5C above, the applicator 16 can provide a generally curved segment 88 of the nonlinear pattern of the first web 12 on the base web 14. As the third guide roller 34 reaches its position as described above with respect to FIG. 5D, the applicator 16 can briefly pause and guide and apply the first web 12 to the base 14 to form an apex 90 of the nonlinear pattern of the first web 12 on the base web 14. As the applicator 16 moves the third guide roller 34 cross directionally to the left (which occurs by rotating the pivot shaft 28 in a counter-clockwise direction) and pivots the third guide roller 34 with respect to the lower cantilever arm 22 to maintain the angle θ to match the instantaneous angle of the first web 12 as described above, the applicator 16 can provide a generally curved segment 92 of the nonlinear pattern of the first web 12 on the base web 14. When the third guide roller 34 reaches the position described above with respect to FIG. 5A, the applicator 16 can provide another generally linear segment 86 of the nonlinear pattern of the first web 12 on the base web 14.

The applicator 16 is adapted to apply the first web 12 to the base web 14 with significant curvature while the base web 14 is traveling at high line speeds. As used herein, "significant curvature" refers to the acute angle α defined by a line tangent to the elastic curve and the longitudinal centerline of the web that is greater than about 45 degrees (see FIG. 6). It is conceived that the nonlinear pattern of the first web 12 on the base web 14 can have curved segment 88 be a mirror image of curved segment 92. It is also conceived that the nonlinear pattern of the first web 12 on the base web 14 can be configured such that the generally curved segment 88 can have a different curvature or acute angle α than the generally curved segment 92.

After the first web 12 is overlaid on the adhesive 77 and applied to the base web 14, the first web 12 and the base web 14 are pulled into the nip 74 by the rotation of the anvil rolls 70, 72. The anvil rolls 70, 72 can apply a predetermined pressure to the first web 12, the adhesive 77, and the base web 14 as they pass through the nip 14 to facilitate adhesive bonding of the first web 12 to the base web 14.

In one suitable embodiment, a distance D (see FIG. 3A) between the third guide roller 34 and the nip 74 is minimized to inhibit misalignment of the first web 12 relative to the base web 14 before the first web 12 is adhesively bonded to the base web 12 (see FIG. 2). Suitably, the distance D between the third guide roller 34 and the nip 74 is less than about 60 millimeters and suitable between about 20 millimeters and about 50 millimeters.

One suitable embodiment of the resulting composite (i.e., the base web 14 having the first web 12 adhered thereto by adhesive 77) is illustrated in FIG. 6. As seen therein, the first web 12 has a width that is greater than a width of the adhesive 77. It is contemplated that the widths of the first web 12 and adhesive 77 can be substantially equal.

The composite can be used in the manufacture of absorbent articles (e.g., diapers, training pants, inconstancy articles). In one particularly suitable configuration, the base web 14 can be used to form outer covers of absorbent articles and the first web 12 can be used to form leg elastics of the absorbent articles. One such absorbent article is illustrated in FIG. 7 in the form of an incontinence garment 100.

Figure 7:
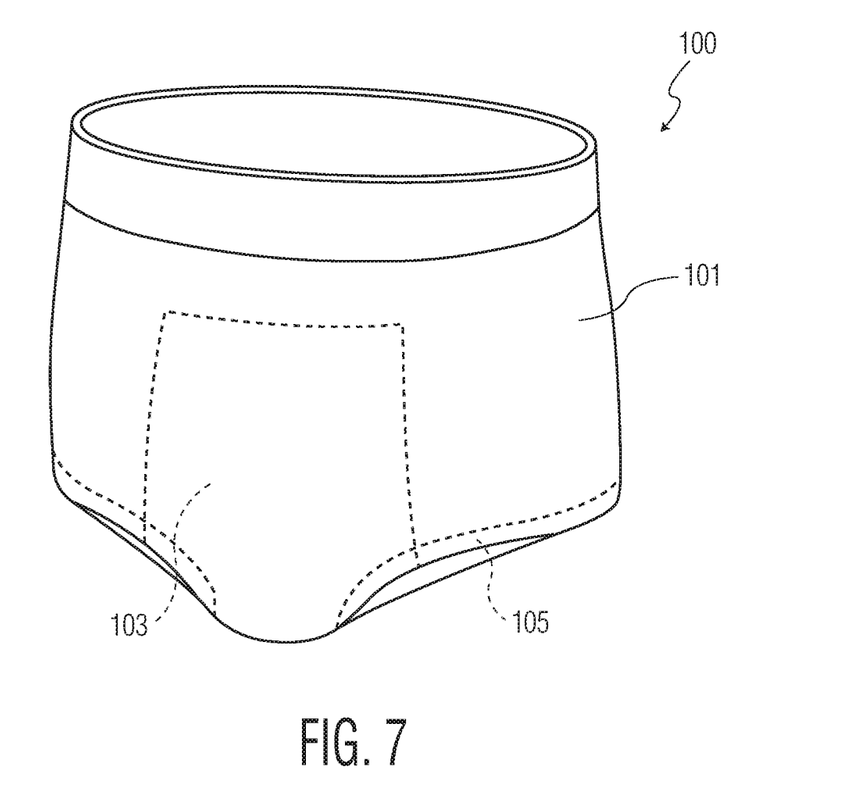
FIG. 7 illustrates a perspective view of one embodiment of an absorbent article in the form of an incontinence garment.

As seen in FIG. 7, the incontinence garment 100 comprises an outer cover 101, an absorbent core 103, and leg elastics 105. The outer cover 101 can be made from the base web 14 and the leg elastics can be defined by the first web 12. It is understood that the garment 100 can include numerous other components (e.g., a bodyside liner, fasteners) other than those illustrated and described herein.

EMBODIMENTS

Embodiment 1

An applicator for guiding a first web to a base web as the base web is advanced in a machine direction, the applicator comprising: a support structure; a cantilever arm supported by the support structure and moveable through a range of motion relative to the support structure in a cross machine direction; a guide roller for guiding the first web onto the base web, the guide roller being pivotally mounted on the cantilever arm for pivotal movement of the guide roller with respect to the cantilever arm; and a connecting link operatively coupled to the guide roller; wherein pivotal movement of the guide roller is dependent on movement of the connecting link, and positioning of the guide roller in the cross machine direction is dependent on movement of the cantilever arm.

Embodiment 2

The applicator of embodiment 1, further comprising a guide shaft operatively connected to the connecting link to move the connecting link in a machine direction.

Embodiment 3

The applicator of embodiment 2, further comprising a guide motor, the guide motor including the guide shaft, the guide motor being a servo motor.

Embodiment 4

The applicator of embodiment 2 or embodiment 3, further comprising a guide arm, the guide arm being operably connected to the guide shaft and the connecting link.

Embodiment 5

The applicator of embodiment 4, wherein the guide arm comprises an attachment end affixed to the guide shaft, a free end, and an intermediate portion extending between the attachment end and the free end, a proximal end of the connecting link being coupled to the guide arm adjacent the free end of the guide arm.

Embodiment 6

The applicator of any one of the preceding embodiments, further comprising a pivot shaft, the cantilever arm being mounted to and extending outward from the pivot shaft.

Embodiment 7

The applicator of embodiment 6, further comprising a pivot motor, the pivot motor including the pivot shaft, the pivot motor being a servo motor.

Embodiment 8

The applicator of embodiment 6 or embodiment 7, wherein the cantilever arm comprises an attachment end affixed to the pivot shaft, a free end, and an intermediate portion extending between the attachment end and the free end, the guide roller being mounted to the cantilever arm adjacent the free end of the cantilever arm.

Embodiment 9

The applicator of any one of the preceding embodiments, wherein the guide roller comprises a bracket, a shaft supported by the bracket, and a roller rotatably mounted on the shaft, the bracket being pivotally mounted to the cantilever arm via a pivot pin and being pivotally mounted to the connecting link.

Embodiment 10

An apparatus for bonding a first web in a nonlinear pattern to a base web, the apparatus comprising: a base web source for feeding the base web to the apparatus; an adhesive applicator for applying adhesive in a pattern to the base web; and the applicator according to embodiment 1, the applicator being configured to deliver and place the first web in the nonlinear pattern on the base web such that the first web overlies the adhesive applied to the base web.

Embodiment 11

The apparatus of embodiment 10, wherein the applicator further comprises a guide arm and a guide motor, the guide motor being operably connected to the guide arm adjacent an attachment end of the guide arm and the connecting link being operably connected to the guide arm adjacent a free end of the guide arm.

Embodiment 12

The apparatus of embodiment 10 or 11, wherein the applicator further comprises a pivot motor, the pivot motor being operably connected to the cantilever arm adjacent an attachment end of the cantilever arm and the guide roller being operably connected to the cantilever arm adjacent a free end of the cantilever arm.

Embodiment 13

The apparatus of any one of embodiments 10-12, wherein the guide roller comprises a bracket, a shaft supported by the bracket, and a roller rotatably mounted on the shaft, the bracket being pivotally mounted to the cantilever arm via a pivot pin and being fixedly mounted to the connecting link.

Embodiment 14

A method for guiding a first web to a base web in a nonlinear pattern, the method comprising: providing the first web; providing the base web; advancing the base web in a machine direction; providing an applicator comprising: a cantilever arm supported by the support structure and moveable through a range of motion relative to the support structure in a cross machine direction; a guide roller configured for engaging the first web; and a connecting link operatively coupled to the guide roller; wherein pivotal movement of the guide roller is dependent on movement of the connecting link; guiding the first web to the base web in a nonlinear pattern by moving the guide roller through a range of motion relative to the support structure in a cross machine direction by moving the cantilever arm and moving the connecting link in a machine direction to pivot the guide roller with respect to the cantilever arm to guide the first web to the base web.

Embodiment 15

The method of embodiment 14, wherein moving the cantilever arm includes rotating the cantilever arm in a reciprocating arc motion.

Embodiment 16

The method of embodiment 14 or 15, wherein the movement of the cantilever arm is controlled by a pivot motor, the pivot motor comprising a pivot shaft coupled to the cantilever arm, the pivot motor being a servo motor.

Embodiment 17

The method of any one of embodiments 14-16, wherein moving the connecting link in a machine direction is controlled by a guide motor, the guide motor comprising a guide shaft coupled to the connecting link, the guide motor being a servo motor.

Embodiment 18

The method of any one of embodiments 14-17, wherein the guide roller comprises a bracket, a shaft supported by the bracket, and a roller rotatably mounted on the shaft, the bracket being pivotally mounted to the cantilever arm via a pivot pin and being pivotally mounted to the connecting link.

Embodiment 19

The method of any one of embodiments 14-18, further comprising: providing an adhesive applicator; applying adhesive to the adhesive in a pattern to the base web; and placing the first web in the nonlinear pattern on the base web such that the first web overlies the adhesive applied to the base web.

Embodiment 20

The method of any one of embodiments 14-19, further comprising: providing a nip; and bonding the first web to the base web by passing the first web and the base web through the nip.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. An applicator for guiding a first web to a base web as the base web is advanced in a machine direction, the applicator comprising:
    a support structure;
    a pivot shaft;
    a cantilever arm supported by the support structure and mounted to and extending outward from the pivot shaft wherein the cantilever arm compries an attachment end affixed to the pivot shaft, a free end, and an intermediate portion extending between the attachment end and the free end, and wherein the cantilever arm is moveable through a range of motion relative to the support structure in a cross machine direction;
    a guide roller for guiding the first web onto the base web, the guide roller being pivotally mounted on the cantilever arm adjacent the free end of the cantilever arm for pivotal movement of the guide roller with respect to the cantilever arm; and
    a connecting link operatively coupled to the guide roller; wherein pivotal movement of the guide roller is dependent on movement of the connecting link, and positioning of the guide roller in the cross machine direction is dependent on movement of the cantilever arm.

2. The applicator of claim 1, further comprising a guide shaft operatively connected to the connecting link to move the connecting link in a machine direction.

3. The applicator of claim 2, further comprising a guide motor, the guide motor including the guide shaft, the guide motor being a servo motor.

4. The applicator of claim 2, further comprising a guide arm, the guide arm being operably connected to the guide shaft and the connecting link.

5. The applicator of claim 4, wherein the guide arm comprises an attachment end affixed to the guide shaft, a free end, and an intermediate portion extending between the attachment end and the free end, a proximal end of the connecting link being coupled to the guide arm adjacent the free end of the guide arm.

6. The applicator of claim 1, further comprising a pivot motor, the pivot motor including the pivot shaft, the pivot motor being a servo motor.

7. The applicator of claim 1, wherein the guide roller comprises a bracket, a shaft supported by the bracket, and a roller rotatably mounted on the shaft, the bracket being pivotally mounted to the cantilever arm via a pivot pin and being pivotally mounted to the connecting link.

8. An apparatus for bonding a first web in a nonlinear pattern to a base web, the apparatus comprising:
    a base web source for feeding the base web to the apparatus;
    an adhesive applicator for applying adhesive in a pattern to the base web; and
    the applicator according to claim 1, the applicator being configured to deliver and place the first web in the nonlinear pattern on the base web such that the first web overlies the adhesive applied to the base web.

9. The apparatus of claim 8, wherein the applicator further comprises a guide arm and a guide motor, the guide motor being operably connected to the guide arm adjacent an attachment end of the guide arm and the connecting link being operably connected to the guide arm adjacent a free end of the guide arm.

10. The apparatus of claim 9, wherein the applicator further comprises a pivot motor, the pivot motor being operably connected to the cantilever arm adjacent an attachment end of the cantilever arm and the guide roller being operably connected to the cantilever arm adjacent a free end of the cantilever arm.

11. The apparatus of claim 8, wherein the guide roller comprises a bracket, a shaft supported by the bracket, and a roller rotatably mounted on the shaft, the bracket being pivotally mounted to the cantilever arm via a pivot pin and being pivotally mounted to the connecting link.

12. A method for guiding a first web to a base web in a nonlinear pattern, the method comprising:
    providing the first web;
    providing the base web;
    advancing the base web in a machine direction;
    providing an applicator comprising:
        a cantilever arm supported by a support structure and moveable through a range of motion relative to the support structure in a cross machine direction;
        a guide roller configured for engaging the first web; and
        a connecting link operatively coupled to the guide roller; wherein pivotal movement of the guide roller is dependent on movement of the connecting link;
    guiding the first web to the base web in a nonlinear pattern by moving the guide roller through a range of motion relative to the support structure in a cross machine direction by moving the cantilever arm and moving the connecting link in a machine direction to pivot the guide roller with respect to the cantilever arm to guide the first web to the base web, wherein moving the cantilever arm includes rotating the cantilever arm in a reciprocating arc motion.

13. The method of claim 12, wherein the movement of the cantilever arm is controlled by a pivot motor, the pivot motor comprising a pivot shaft coupled to the cantilever arm, the pivot motor being a servo motor.

14. The method of claim 12, wherein moving the connecting link in a machine direction is controlled by a guide motor, the guide motor comprising a guide shaft coupled to the connecting link, the guide motor being a servo motor.

15. The method of claim 12, wherein the guide roller comprises a bracket, a shaft supported by the bracket, and a roller rotatably mounted on the shaft, the bracket being pivotally mounted to the cantilever arm via a pivot pin and being pivotally mounted to the connecting link.

16. The method of claim 12, further comprising:
    providing an adhesive applicator;
    applying adhesive in a pattern to the base web; and
    placing the first web in the nonlinear pattern on the base web such that the first web overlies the adhesive applied to the base web.

17. The method of claim 16, further comprising:
    providing a nip; and
    bonding the first web to the base web by passing the first web and the base web through the nip.

* * * * *